(12) United States Patent
Lin

(10) Patent No.: US 11,767,968 B2
(45) Date of Patent: Sep. 26, 2023

(54) BUNDLE BEAM UV LED ULTRAVIOLET LIGHT SWEEPING METHOD AND DEVICE THEREOF

(71) Applicant: Hsien-Sheng Lin, Taipei (TW)

(72) Inventor: Hsien-Sheng Lin, Taipei (TW)

( * ) Notice: Subject to any disclaimer, the term of this patent is extended or adjusted under 35 U.S.C. 154(b) by 8 days.

(21) Appl. No.: 17/746,979

(22) Filed: May 18, 2022

(65) Prior Publication Data
US 2023/0102963 A1    Mar. 30, 2023

(30) Foreign Application Priority Data

Sep. 14, 2021 (TW) ................. 110134264

(51) Int. Cl.
| | | |
|---|---|---|
| F21V 14/04 | (2006.01) |
| F21V 7/04 | (2006.01) |
| F21V 7/00 | (2006.01) |
| F21K 9/68 | (2016.01) |
| B29C 35/08 | (2006.01) |
| F21Y 115/10 | (2016.01) |

(Continued)

(52) U.S. Cl.
CPC ............... *F21V 14/04* (2013.01); *F21K 9/68* (2016.08); *F21V 7/0066* (2013.01); *F21V 7/0083* (2013.01); *F21V 7/048* (2013.01); *A01G 9/249* (2019.05); *A61L 2/10* (2013.01); *B29C 35/0805* (2013.01); *B29C 2035/0827* (2013.01); *F21Y 2115/10* (2016.08)

(58) Field of Classification Search
CPC ...... F21V 14/04; F21V 7/0066; F21V 7/0083; F21V 7/048; F21K 9/68; A01G 9/249; A61L 2/10; B29C 35/0805; B29C 2035/0827; F21Y 2115/10; F21Y 2103/33; Y02P 60/14
See application file for complete search history.

(56) References Cited

U.S. PATENT DOCUMENTS

2006/0268556 A1* 11/2006 Hsieh ................. F21V 7/048
                                                                362/347
2008/0067425 A1*  3/2008 Kaszuba ......... H01L 21/67115
                                                            250/492.2

(Continued)

FOREIGN PATENT DOCUMENTS

CN      110006007 A  *  7/2019

*Primary Examiner* — Elmito Breval
(74) *Attorney, Agent, or Firm* — Leong C. Lei

(57) ABSTRACT

A bundle beam UV LED ultraviolet light sweeping method includes: activating electrical power to input into a PCB to light up a bundle beam UV LED ultraviolet light bead and driving a motor to cause a polygonal multiple-reflective-surface aluminum mirror to rotate, ultraviolet light from the UV LED being projected toward the reflective surface, and reflected by the reflective surface to change light direction for successive back-and-forth home-position-returning sweeping, the light converting from lines into sectorial shapes that are connected to form a large ultraviolet light operation region. The device includes a rotating device having a motor of which a spindle is mounted with a polygonal multiple-reflective-surface aluminum mirror; an UV LED bundle beam light source assembly having a bundle beam UV LED ultraviolet light bead fixed on a PCB; and a fixing base having a main body and a plurality of mounting braces.

18 Claims, 13 Drawing Sheets

(51) Int. Cl.
*A61L 2/10* (2006.01)
*A01G 9/24* (2006.01)

(56) References Cited

U.S. PATENT DOCUMENTS

2020/0215213 A1* 7/2020 Bryant .................. G06F 1/1601
2021/0244839 A1* 8/2021 Trapani .................... A61L 2/24

* cited by examiner

BUNDLE BEAM UV LED ULTRAVIOLET LIGHT SWEEPING METHOD AND DEVICE THEREOF

TECHNICAL FIELD OF THE INVENTION

The present invention relates to a bundle beam ultraviolet light-emitting diode (UV LED) ultraviolet light sweeping method and its device thereof, of which the method mainly employs bundle beam UV LED ultraviolet light bead to supply a high-dosage radiation intensity, which is then subjected to sweep to expand the high radiation dosage utilizable area, and is further arranged in a reflection chamber for repeated reflection realizable by the reflection chamber to make multiple use of the reflected ultraviolet light to enhance the radiation dosage of the ultraviolet light; the device is applicable to sterilization and disinfection of air, or sterilization and disinfection in water, or sterilization and disinfection of surfaces of vessels, or fresh-keeping sweeping on surfaces of foods, cultivation of plants, light therapy sweeping, and supplying of high radiation dosage for applications of UV curing and the likes.

DESCRIPTION OF THE PRIOR ART

Known technology of ultraviolet light (UV) involves mercury-containing radiation light source. Other than its environmental unfriendliness, this light source has a frequency band spreading from 254 nm to visible light. In this wide range of wavelength, only very small range, or that of 250-285 nm is applicable to sterilization and only that of 350-405 nm is applicable to light curing. Thus, the energy is wasted tremendously outside these specific wavelength ranges. An UV LED is a single band thus uses less electricity. UV LED is, therefore, beginning to be used as a sterilization radiation source. These radiation light source devices, however, are typically arranged in a fixed manner, or a static multiple-bead arrayed distribution, in which the distribution is made in a high density, the radiation dosage, however, is of poor homogeneity. The cause of this common result can be found in the definition of a radiation angle of an LED whereas an illumination angle being an included angle between luminance of the center axis and luminance of 50% decay (see FIG. 1), and inhomogeneity of 50% light radiation exists between light of the center axis and light of one side. It would be difficult for the known technology to achieve homogeneity of light.

The known technology does not possess the ability to offer high radiation dosage for long distance and large area applications. For example, when projection is made for a distance of 2 centimeters from a 20×20 mil UV LED bead with 120-degree illumination angle; the bead area or the area at the origin of UV LED light projection is 20×20 mil=0.258 $mm^2$, length of the base of the isosceles triangle of the 120-degree projection at 2 centimeters is 69.788 mm, the sectional area of the projection is 69.788×69.788=4870.36 $mm^2$, the sectional area ratio between bead area and the sectional area at 2 centimeters of the projection is 0.258/4870.36=0.000053, which means if the radiation intensity at the origin of the bead is 1 $mw/cm^2$ and the radiation intensity being equally distributed to the sectional area at 2 centimeters, the radiation intensity of unit area becomes 0.000053 $mw/cm^2$. The radiation intensity and the projection distance or the sectional area at the distance are inversely proportional. The projection distance and the sectional area at the distance, therefore, cast significant influences to the radiation intensity. The known application of UV LED to curing of light cure base materials face the dilemma of decreased radiation intensity in enlarged field or area of application required. One known approach to solve the problem is to increase light power to achieve curing in desired time. The common consequence of that approach is that materials are subjected to radiation heat and becomes scorching, wherein vaporized tiny particles contaminate the UV beads. Scorching can be prevented by increasing the distance, but a disadvantageous consequence is an incompletely-cured sticky surface.

The known technology of reflective scanning is most applied to text or image capturing and/or inputting devices. Thus, the device includes two components: (1) a light source and (2) a photosensor, like in a charge-coupled device (CCD). In such process of scanning coordinate, light vectors in X-axis and Y-axis are required, and a Z-axis position is also needed for display the entire outline of a text or an image; laser is the primary light source, and the laser should be parallel to the scanned target to achieve its purpose in image processing, such as photocopy machine or iris recognition scanning. The sweeping method in the present invention, since its purpose is only to provide ultraviolet light energy for disinfection and sterilization, or to supply photopolymerization energy, or to assist synthesis of vitamin D, only linear vector sweeping of a light source is required, and no X-axis, Y-axis, nor Z-axis position orientation for repeated origin-returning positional sweeping. The bundle beam UV LED ultraviolet light radiation beam area directly works without photosensor recording and without image capturing input device. Therefore, there would be angles between the position of the light source and the scanned target.

In view of the above, the inventor devotes a huge amount of energy and spirit for development and search, for the purpose of continuous breakthrough and innovation in the field, in order to provide a novel measure to handle the deficiency of the known technology, which, in addition to a more benignant product for the society, offers better efficient removal of viruses and improved protection to human beings, and also helps enhance development of the UV LED industry.

SUMMARY OF THE INVENTION

An objective of the present invention is to provide a bundle beam UV LED ultraviolet light sweeping method and device thereof, wherein the method is a method in which a polygonal shaped multiple-reflective-surface aluminum mirror is put into rotation to change the projection direction of ultraviolet light facet for cyclical and successive home-position-returning positional sweeping that converts UV light from a line into a sectorial area to expand a light beam region widening ranges of product applications. In addition, the device employs a bundle beam UV LED bead to provide a high dosage radiation ultraviolet light source, lengthen and widen the effective ultraviolet light beam region sweep range. Furthermore, the bundle beam UV LED ultraviolet light sweeping device is applicable to sterilization and disinfection of microorganism viruses, oxidization of organic gases for deodorization, polymerization of organic liquids containing photo-initiators, synthesis of vitamin D for assisting growth of fungi and mushrooms, and phototherapy of skins for treating skin diseases.

Ultraviolet light sterilization is the best ideal measure for sterilization, disinfection, fresh-keeping, and cultivation, and is also the best way of photocuring of UV resins. According to Grotthuss-Draper Law of photochemical principle, (1) a chemical reaction only occurs for a spectral wavelength that can be absorbed. The weave peak effective absorption frequency bandwidth for the DNAs and RNAs of bacteria or microorganisms is around 250-285 nm, and this is the best waveband section for sterilization and disinfection. (2) The radiation dosage must be greater than the effective activation energy, so that when the viruses absorb an amount that is greater than the lethal radiation dosage, the bacteria can then be killed, or disinfected or sterilized through bond breaking. For example, for fecal coliform, K=lethal dosage 6600 $\mu W/cm^2$, and based on the formula K=I (intensity $\mu W/cm^2$)*t (time-sec), where I is radiation intensity of irradiation, killing bacteria in seconds is possible if I is high enough. When the radiation is lower than 70 $\mu W/cm^2$, the bacteria may implement a repairing function, which is referred to as ineffective sterilization. Thus, the UV LED radiation wavelength region must be corresponding thereto and must have a radiation intensity that is high enough, in order to effectively and efficiently kill bacteria and disinfect and sterilize in a manner of being safe without secondary contamination. UV resins are often added with 350-405 nm photo-initiators (light absorber region), and fast curing may be realized by supplying UV radiation of a corresponding wavelength. Further, 280-350 nm could be applied to phototherapy and plant cultivation and helps synthesis of vitamin D.

To achieve the above objective, the present invention provides a bundle beam UV LED ultraviolet light sweeping method, of which sweeping steps are as follows: activating electrical power to input into a PCB to light up a bundle beam UV LED ultraviolet light bead and also drive a motor to cause a polygonal multiple-reflective-surface aluminum mirror mounted on a motor spindle to rotate; projecting a bundle beam of ultraviolet light toward the reflective surface aluminum mirror in rotation so that the ultraviolet light is reflected by the aluminum reflective mirror in rotation to change the direction of the light for successive back-and-forth home-position-returning sweeping; and the UV light converting from lines to sectorial shapes, the multiple sectorial shapes being connected to form a large ultraviolet light beam region, this being referred to as the bundle beam UV LED ultraviolet light sweeping method.

To achieve the above objectives, the present invention provides a bundle beam UV LED ultraviolet light sweeping device, which at least comprises a rotating device, an UV LED bundle beam light source assembly, and a fixing base, wherein the rotating device comprises a motor and a polygonal multiple-reflective-surface aluminum mirror, the polygonal multiple-reflective-surface aluminum mirror being mounted to a spindle of the motor, the spindle and the polygonal multiple-reflective-surface aluminum mirror being mounted in a hole-to-hole fitting or being fit with additionally added with a universal joint to eliminate centerline offset between the two; further, the UV LED bundle beam light source assembly comprises at least one bundle beam UV LED ultraviolet light bead and a PCB, the bundle beam UV LED ultraviolet light bead being fixed on the PCB; further, the fixing base comprises a main body and a plurality of mounting braces, the main body of the fixing base carrying the components, the main body and the mounting braces being integrally formed as a unity or being separate parts, one of the mounting braces being provided with an electrical power inlet hole. The fixed base can be one of an organic material coated with a metallic material, an inorganic material, and a metallic material.

The bundle beam UV LED ultraviolet light sweeping device according to the present invention further comprises a reflection chamber, the reflection chamber being a circular shape, a square shape or an irregular shape having a high reflectivity layer of aluminum. The swept and projected ultraviolet light projecting from an UV LED travels as being reflected by the high reflectivity aluminum of the reflection chamber to return in a direction toward the fixing base, being subjected to multiple successive re-direction and reflection until the radiation light varnishes, the reflection chamber helps enhance re-use of the radiation light shortening sterilization time. A drawback of ultraviolet light sterilization being that for light travels in a straight line, bacteria hidden behind dust that is on the side opposite to light can escape. By repeatedly changing the direction of the UV light, escape of the bacteria can be avoided, and this is the unique effect provided by the present invention.

The bundle beam UV LED ultraviolet light sweeping device according to the present invention further comprises a lateral-opening type reflection chamber, and the lateral-opening type reflection chamber includes a lateral opening to allow radiation light projects outwards through the opening for surface sterilization of medical equipment and fresh-keeping and preservation of foods, wherein radiation width or area is determined by an angular size and a length of the lateral opening of the lateral-opening type reflection chamber. (FIG. 8)

In the bundle beam UV LED ultraviolet light sweeping device according to the present invention, the bundle beam UV LED ultraviolet light bead is a traditional 250-405 nm UV LED primary encapsulation ultraviolet light bead, added with secondary encapsulation of a hollow metal tube having a height of 1.2 mm to 20 mm, and the greater the height, the smaller the light emission angle and the more concentrated the light intensity, and the length can be changed according to requirement, and the UV LED 250-405 nm bead is not a laser beam and is dependent on internal reflection of a hollow internal metal mirror surface to change the travel direction of the radiation light and overlapping of light to realize homogeneity, and the opening size of the hollow metal tube constrains the light shape and makes the light uniform and concentrated to be referred to as "bundle beam", the inventor of present invention realizes the principle of the Maddox rod can be applied here to control the direction of UV light reflection and the hollow metal tube can be further processed so as to form, in a direction perpendicular to a surface of radiation light emitting from a dice, a successive internal corrugated triangular configuration column shaped reflection mirror as shown in sectional view FIG. 3e, or a successive internal corrugated rectangular configuration column shaped reflection mirror as shown in sectional view FIG. 3f, or a successive internal corrugated arc configuration aluminum reflection mirror as shown in sectional view FIG. 3d, the radiation light is projected outwards in a direction perpendicular to a dice surface, and the reflection light forms a meridian surface focusing line perpendicular to the successive column shape reflection mirror, so as to form a bundle beam UV LED ultraviolet light bead that provides bundle beam straight extending in a direction parallel to the dice light source, and such a bundle beam is further subject to constraint of the secondary optical by a hollow metal tube to change angle and travel direction of light to form concentration of light for excellent light homogeneity, and the travel direction is parallel to the straight extension direction of the hollow metal tube, the angle being small for being suitable for long distance sweeping, and also providing a high ultraviolet light radiation dosage beam, and secondary encapsulation can be realized with the inside-rectangular and outside rectangular, or inside-circular and outside-circular, or inside-circular and outside-rectangular hollow metal tube, and the hollow metal can be one of aluminum, copper, nickel, tin, or a metal coated with aluminum powder and is fixed on the PCB to serve as an ultraviolet light radiation light source assembly used in the bundle beam UV LED ultraviolet light sweeping method according to the present invention.

In the bundle beam UV LED ultraviolet light sweeping device according to the present invention, the rotating device is a device for driving the polygonal multiple-reflective-surface aluminum mirror, and the polygonal multiple-reflective-surface aluminum mirror requires at least three or more than three reflective aluminum surface mirrors, and the motor for rotating power of the rotating device is one of an alternate-current motor, a direct-current motor, a brushless motor, or a servo motor, and the polygonal multiple-reflective-surface aluminum mirror is fit over and mounted to the spindle of the motor, and the polygonal surface forms, with respect to a side surface of the reflective surface, an included angle θ, see FIG. 4, and the two jointly form the rotating device.

In the bundle beam UV LED ultraviolet light sweeping device according to the present invention, the fixing base comprises a main body and a plurality of mounting braces, and the main body of the fixing base fixes the rotating device, and the UV LED bundle beam light source assembly, and the main body and the mounting braces can be integrally formed as a unit or are separate parts, and one of the mounting braces is provided with an electrical power inlet hole, and the mounting braces are mountable inside the aluminum reflection chamber. Further, the material of the fixing base can be one of an inorganic material, an organic material, or a metallic material. The main body of the fixing base is provided with mounting bolt holes for the motor and the PCB of the rotating device, and the fixing base comprises the plurality of mounting braces. A substrate of the PCB can be one of a PCB (RF-4 organic material), a MCPCB (metal core PCB), or a ceramic PCB.

In the bundle beam UV LED ultraviolet light sweeping device according to the present invention, when the bundle beam UV LED ultraviolet light bead has a wavelength in the range of 250-285 nm, it exhibits an effect of sterilization and disinfection, and according to the formula of technical standards for sterilization and disinfection, bacterium-killing radiation dosage K=I (radiation intensity μW/cm$^2$)×t (radiation time-sec), and the more intense the radiation dosage, the shorter the time, the two being in inversely proportional to each other. The bundle beam UV LED ultraviolet light bead provides ultraviolet light of a high radiation dosage, exhibiting characteristics of processing massive number of bacteria for sterilization and disinfection in a short period of time, and the radiation light intensity of the bundle beam UV LED ultraviolet light bead is high to reduce decay for long distance projection of the ultraviolet light (see Table 1, The Radiation Intensity Comparison Chart of Illumination Angle VS. Distance from Irradiation Target), is suitable for a long distance high radiation dosage back-and-forth home-position-returning sweeping method, widens processing radiation light operation area, and also making distribution of radiation dosage uniform, has an advantage of including no dead zone in the sweeping operation area.

TABLE 1

| distance from illumination target | 0 cm | 1 cm | 2 cm | 3 cm | 4 cm |
|---|---|---|---|---|---|
| radiation intensity (mW/cm$^2$) for illumination angle of 3 degrees | 469.3 | 444.89 | 425.66 | 412.05 | 401.76 |
| unit area radiation intensity percentage | 100% | 94.8% | 90.7% | 87.8% | 85.6% |
| radiation intensity (mW/cm$^2$) for illumination angle of 120 degrees | 469.3 | 33.12 | 4.14 | 1.68 | 0.027 |
| unit area radiation intensity percentage | 100% | 7.1% | 0.9% | 0.04% | 0.006% |

In the bundle beam UV LED ultraviolet light sweeping device according to the present invention, when the bundle beam UV LED ultraviolet light bead of the present invention has a wavelength of 350-405 nm, it is applicable to photopolymerization and curing, and based on the principle of Einstein's Law of Photochemical Equivalence, the bundle beam UV LED ultraviolet light bead provides high radiation dosage ultraviolet light back-and-forth uniform shifting sweeping, eliminating the need to reduce distance to the objects being cured or correspondingly requires less UV LED power, so that radiation heat is small to thereby prevent UV resin from being easily scorched, and the low molecule UV resin is not readily vaporized to contaminate the bead, and the influence of heat is reduced to prevent scorching and odor, and an advantage of smoothness and low radiation heat of the product.

In the bundle beam UV LED ultraviolet light sweeping device according to the present invention, the polygonal surface of the polygonal multiple-reflective-surface aluminum mirror forms, with respect to the side surface of each of the reflective surfaces, a ƒ included angle, and when the θ included angles of the reflective surfaces are all identical θ angles for each of the reflective surfaces, the at least one bundle beam UV LED ultraviolet light bead on the PCB projects ultraviolet light so emitted toward the reflective surfaces of the polygonal multiple-reflective-surface aluminum mirror, and the light beam is reflected by the reflective surface to form a uniformly distributed planar UV beam region, as shown in FIG. 5a.

In the bundle beam UV LED ultraviolet light sweeping device according to the present invention, the polygonal surface is connected to a side surface of the reflective surface of the polygonal multiple-reflective-surface aluminum mirror to form an angle θ that is different for each of the surfaces, as shown in FIGS. 4a, 4b, and 4c, and the at least one bundle beam UV LED ultraviolet light bead on the PCB projects a light beam so emitted toward the side surfaces of the reflective surfaces of the polygonal multiple-reflective-surface aluminum mirror, and each light beam is reflected as reflection light having a different angle θ for each one of the reflective surfaces and a Z-axis height is increased, and the reflection light beam forms a uniformly distributed 3D UV light beam region, as shown in FIG. 5b.

The bundle beam UV LED ultraviolet light sweeping method and the device thereof according to the present invention provide the following advantages:

(1) providing UV high radiation dosage for killing bacteria in second.
(2) enabling long distance projection of radiation dosage (Table 1).
(3) enabling large area uniform sweeping and projection of high homogeneity radiation dosage.
(4) enhancing unit area radiation dosage of ultraviolet light and reducing radiation heat.
(5) enabling no-dead-zone high radiation dosage leftward-rightward back-and-forth shifting sweeping as shown in FIG. 5a.
(6) enabling upward-downward, leftward-rightward three-dimensional back-and-forth 3D shifting sweeping, as shown in FIG. 5b, allowing wide range of applications.

DETAILED DESCRIPTION OF THE PREFERRED EMBODIMENT

The present invention provides a bundle beam UV LED ultraviolet light sweeping method and device thereof. To allow those familiar with common knowledge of related fields to fully understand the objective, features, and advantages of the present invention, proper embodiments are illustrated below, with reference to the attached drawings, and a detailed description of the technical contents of the present invention.

Embodiment I: A Bundle Beam UV LED Ultraviolet Light Sweeping Device

Figure 2:
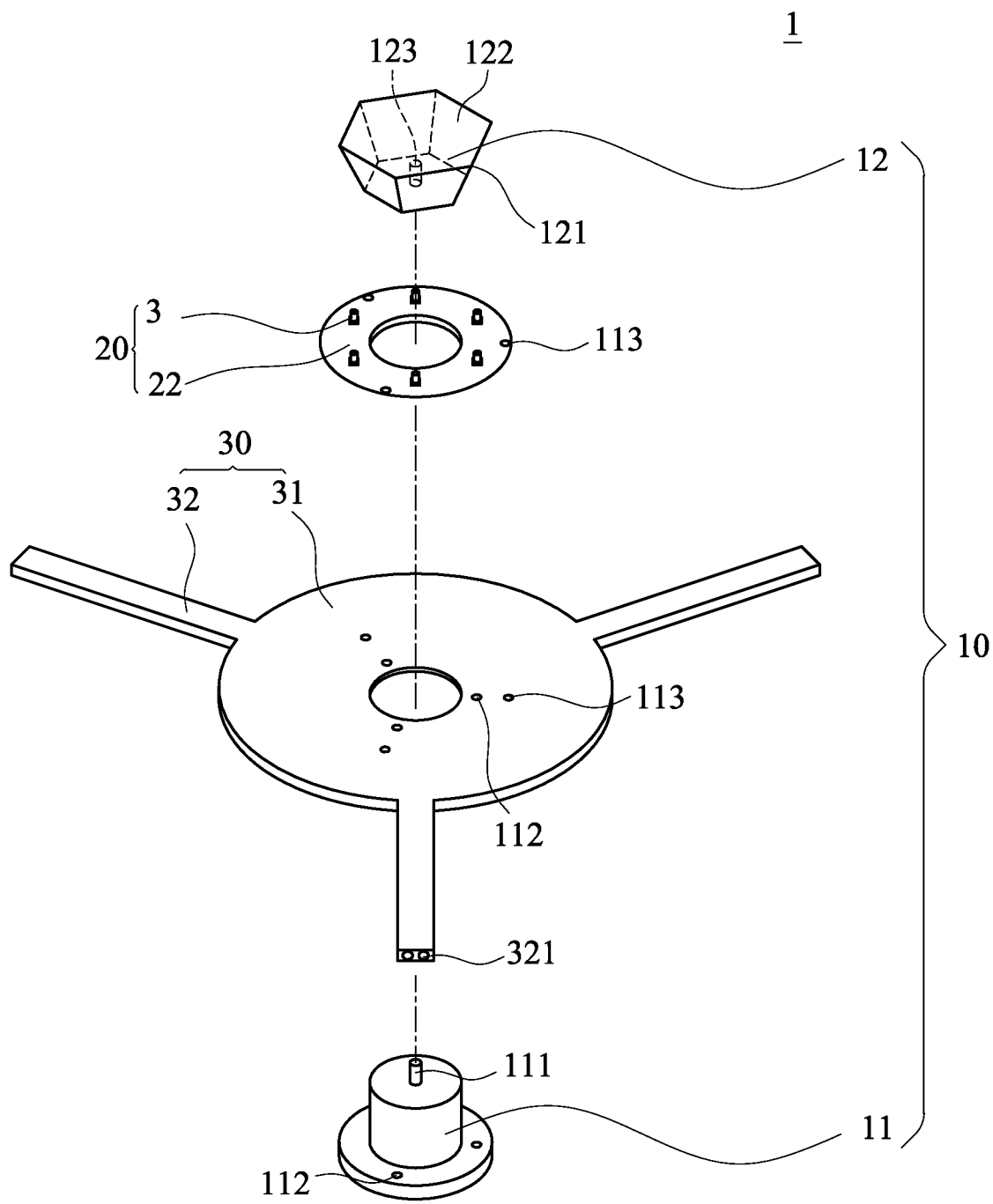
FIG. 2 is an exploded view showing a structure of a bundle beam UV LED ultraviolet light sweeping device according to Embodiment I of the present invention.

Referring to FIG. 2, is an exploded view showing a structure of a bundle beam UV LED ultraviolet light sweeping device according to Embodiment I of the present invention.

Figure 4A:
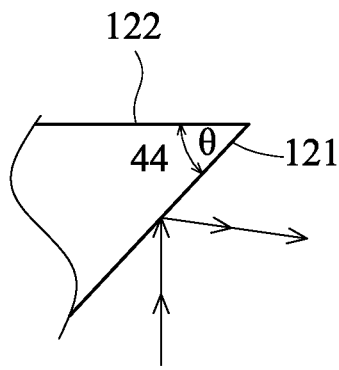
FIGS. 4a-4c are schematic views illustrating various included angles θ between a polygonal surface and a side face of a reflective surface of a polygonal multiple-reflective-surface aluminum mirror according to the present invention.
Figure 4B:
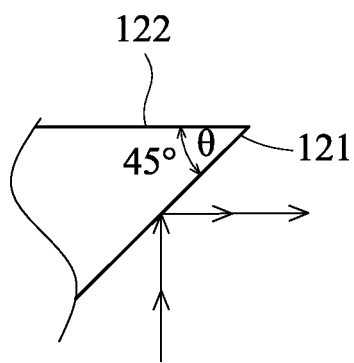
Figure 4C:
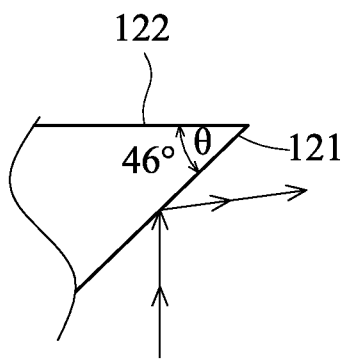

As shown in FIG. 2, the bundle beam UV LED ultraviolet light sweeping device 1 comprises: a rotating device 10, an UV LED bundle beam light source assembly 20, and a fixing base 30. The rotating device 10 includes a motor 11 and a polygonal multiple-reflective-surface aluminum mirror 12 fit to a spindle 111 of the motor 11. Each side of the polygonal multiple-reflective-surface aluminum mirror 12 forms a reflective surface 121. A polygonal surface 122 is formed on a top of the polygonal multiple-reflective-surface aluminum mirror 12. The polygonal surface 122 forms an included angle θ with respect to the multiple reflective surfaces 121, as shown in FIG. 4a. Fitting the polygonal multiple-reflective-surface aluminum mirror 12 to the motor spindle can be done with direct fitting or indirect fitting by means of an intervening universal bearing to eliminate center offset between the spindle and the polygonal multiple-reflective-surface aluminum mirror 12. Next, the UV LED bundle beam light source assembly 20 comprises a PCB 22 and at least one bundle beam UV LED ultraviolet light bead 3 mounted on the PCB 22. Further, the fixing base 30 comprises a main body 31 and a plurality of mounting braces 32. The main body 31 provides a platform for carrying elements, such as mounting of the motor 11 and the PCB 22, in which motor seat bolt holes 112 are provided for mounting the motor 11 on the main body 31 and PCB bolt holes 113 are provided for mounting the PCB 22 on the main body 31. Among the mounting braces 32, one of the mounting braces 32 is provided with an electrical power inlet hole 321. The fixing base 30 is made of either an organic material coated with metallic aluminum, an inorganic material, or a metallic material. The electrical power inlet hole 321 connects with the at least one bundle beam UV LED ultraviolet light bead 3 and the motor 11. When electrical power is activated, the electrical power inputs into the PCB 22, and the motor 11, and also the at least one bundle beam UV LED ultraviolet light bead 3, is activated simultaneously to drive the polygonal multiple-reflective-surface aluminum mirror 12 to rotate therewith, and the bundle beam UV LED ultraviolet light bead 3 on the PCB 22 emits and projects a light beam toward the reflective surface 121 of the polygonal multiple-reflective-surface aluminum mirror 12 and a reflection light beam is projected toward a working region to form a homogeneously distributed sectorial shaped light beam region, and multiple sectorial regions are connected to form a circular, large-area light beam region. The polygonal multiple-reflective-surface aluminum mirror 12 is formed by means of plastic injection molding, followed by being coated with metallic aluminum through vacuum electroplating, or is directly formed by machining or processing one of aluminum, nickel, copper, and zinc. The polygonal multiple-reflective-surface aluminum mirror 12 is formed, in a center thereof, with a fitting aperture 123 for fitting over and fixing to the spindle 111 of the motor 11. The motor 11 can be either one of an alternate-current motor, a direct-current motor, a brushless motor, or a stepping motor.

Figure 3A:
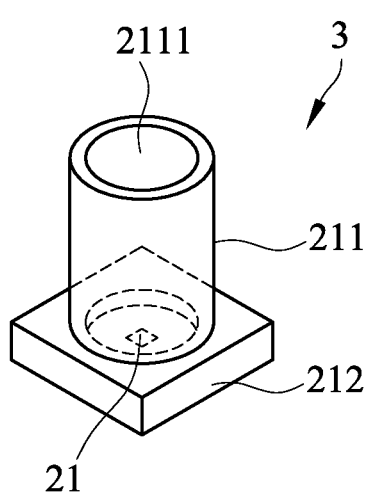
FIG. 3a is a schematic view showing an inside-circular and outside-circular secondary encapsulation hollow metal tube according to the present invention.
Figure 3B:
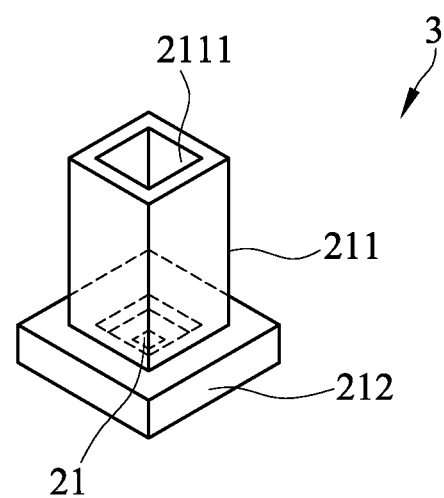
FIG. 3b is a schematic view showing an inside-rectangular and outside-rectangular secondary encapsulation hollow metal tube according to the present invention.
Figure 3C:
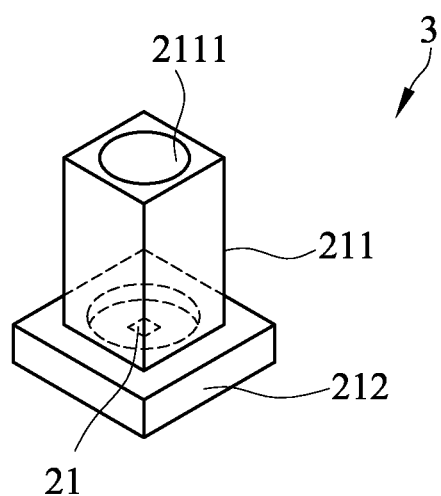
FIG. 3c is a schematic view showing an inside-circular and outside-rectangular hollow metal tube according to the present invention.
Figure 3D:
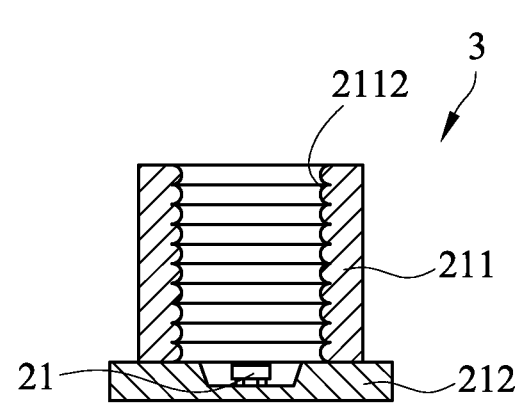
FIG. 3d is a schematic view showing a secondary encapsulation hollow metal tube according to the present invention having an internal mirror surface formed with a successive corrugated arc-configuration column-shaped reflection mirror.
Figure 3E:
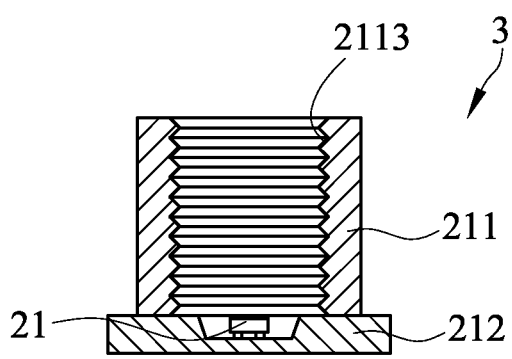
FIG. 3e is a schematic view showing a secondary encapsulation hollow metal tube according to the present invention having an internal mirror surface formed with a successive corrugated triangular-configuration column-shaped reflection mirror.
Figure 3F:
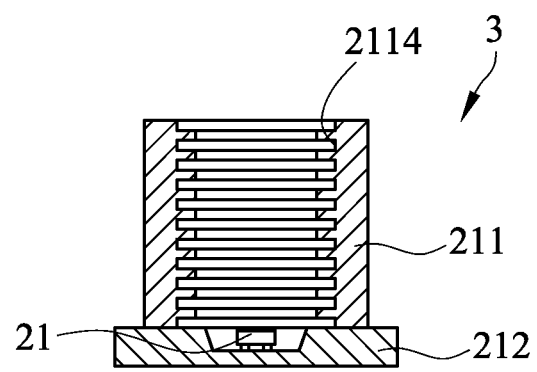
FIG. 3f is a schematic view showing a secondary encapsulation hollow metal tube according to the present invention having an internal mirror surface formed with a successive corrugated rectangular-configuration column-shaped reflection mirror.

Referring to FIGS. 3a-3f, FIG. 3a is a schematic view showing an inside-circular and outside-circular hollow metal tube according to the present invention; FIG. 3b is a schematic view showing an inside-rectangular and outside-rectangular hollow metal tube according to the present invention; FIG. 3c is a schematic view showing an inside-circular and outside-rectangular hollow metal tube according to the present invention; FIG. 3d is a schematic view showing a hollow metal tube according to the present invention having an internal mirror surface formed with a successive corrugated arc-configuration column-shaped reflection mirror; FIG. 3e is a schematic view showing a hollow metal tube according to the present invention having an internal mirror surface formed with a successive corrugated triangular-configuration column-shaped reflection mirror; and FIG. 3f is a schematic view showing a hollow metal tube according to the present invention having an internal mirror surface formed with a successive corrugated rectangular-configuration column-shaped reflection mirror. These secondary encapsulation uses either the inside-rectangular and outside-rectangular shaped hallow metal tube, or the inside-circular and outside-circular shaped hollow metal tube, or the inside-circular and outside-rectangular shaped hollow metal tube, and the material of the hollow metal tube can be either one of aluminum, copper, nickel, tin, or a metal coated with aluminum powder.

As shown in FIGS. 3a-3f, the bundle beam UV LED ultraviolet light bead 3 is such that secondary encapsulation is applied to encapsulate and mount, through application of methyl silicone, a hollow metal tube 211 on a lead frame support 212 on which a traditional ultraviolet light bead 21 of the UV LED is mounted through primary encapsulation, and radiation light is reflected back and forth by a reflective aluminum mirror surface 2111 inside the hollow metal tube 211 to form a homogeneous concentric light beam for outward projection, with a small divergence angle, to project a high radiation dosage. Based on the principle of Maddox rod applied, the hollow metal tube 211 is formed, as a surface perpendicular to radiation light emitting from the dice, a non-spheric column-shape reflective mirror surface 2111 that is a successive internal corrugated arc-configuration column shape 2112, a successive internal corrugated triangular-configuration column shape 2113, a successive internal corrugated rectangular-configuration column shape 2114, and radiation light is perpendicular to the column shaped surface for projecting outward to achieve meridian direct light incidence, forming straight radiation bundle beam UV LED light in a direction perpendicular to a dice surface. The straight light can project further, beam being further converged, to server as a radiation light source of the bundle beam UV LED ultraviolet light bead 3 for a sweeping method.

Figure 5A:
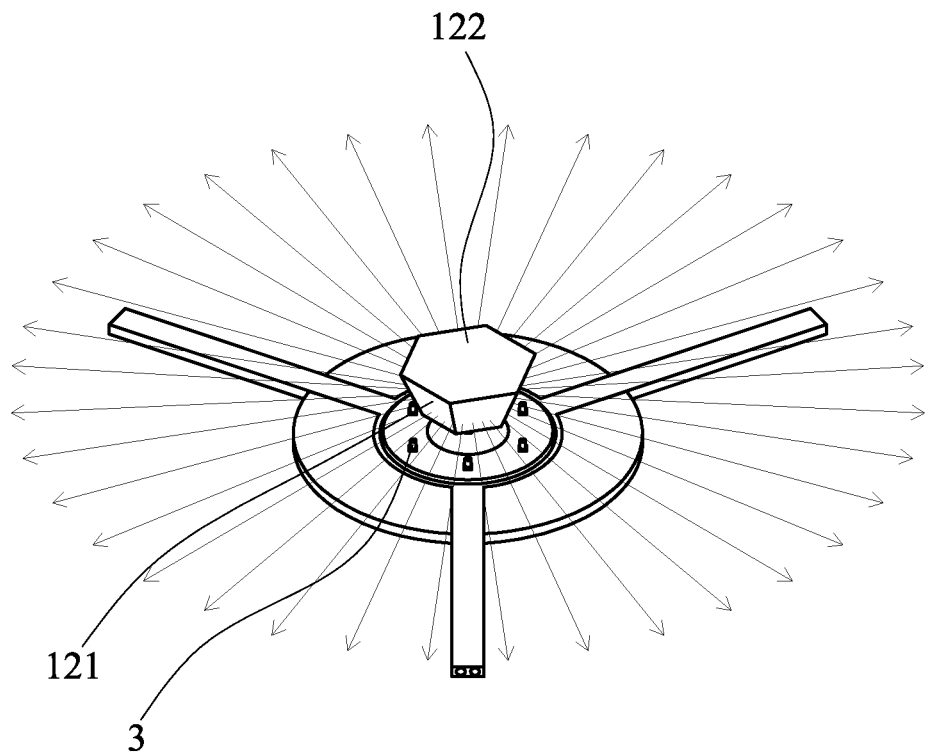
FIG. 5a is a schematic view demonstrating light emission under a condition that the included angles θ between a polygonal surface and side face of reflective surfaces of a polygonal multiple-reflective-surface aluminum mirror are identical for each surface according to the present invention.
Figure 5B:
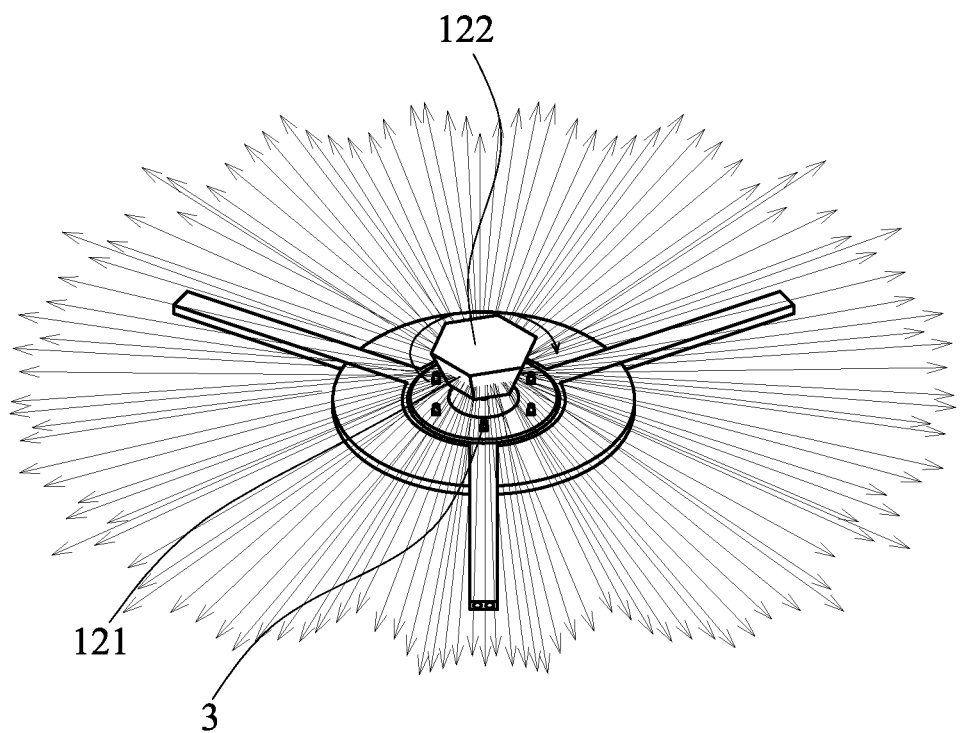
FIG. 5b is a schematic view demonstrating light emission under a condition that the included angles θ between a polygonal surface and side faces of reflective surfaces of a polygonal multiple-reflective-surface aluminum mirror are different for each surface according to the present invention.

Referring to FIGS. 4a-5b, FIGS. 4a-4c demonstrate various included angles θ between the polygonal surface 122 and a side face of the reflective surface of a polygonal multiple-reflective-surface aluminum mirror 121 according to the present invention; and FIG. 5a is a schematic view demonstrating the included angles θ between the polygonal surface 122 and the side faces of the reflective surfaces of the polygonal multiple-reflective-surface aluminum mirror 121 according to the present invention are identical for each surface, and FIG. 5b is a schematic view demonstrating the included angles θ between a polygonal surface 122 and the side faces of the reflective surfaces of the polygonal multiple-reflective-surface aluminum mirror 121 according to the present invention are different for each surface.

As shown in FIG. 2, the polygonal multiple-reflective-surface aluminum mirror 12 includes three or more than three reflective surfaces 121. The included angle θ between the reflective surfaces 121 and the polygonal surface 122 of the polygonal multiple-reflective-surface aluminum mirror 12 can be made identical or different for each of such surfaces. When the included angle θ is identical for each of such surfaces, as shown in FIG. 5a, the reflected ultraviolet light changes from a line to a sectorial shape to thereby expand an operation space; when the included angle θ is different for each of such surfaces, in addition to divergence surfaces form in Y-axis and X-axis, a thickness in Z-axis direction is increased, as shown in FIG. 5b, the operational space of the ultraviolet light increases three dimensionally to provide an enlarged designable space for highly widened application of products.

Figure 6A:
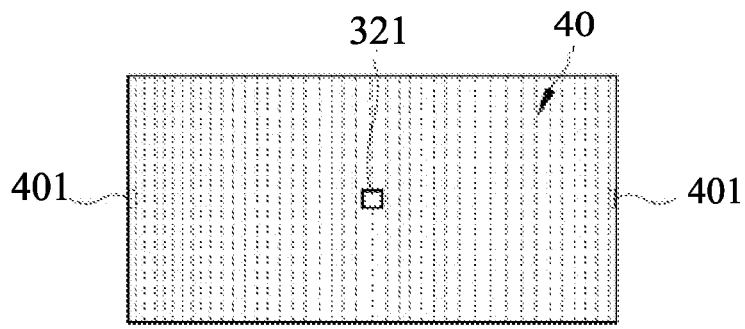
FIG. 6a is a lateral elevational view showing a reflection chamber according to the present invention.
Figure 6B:
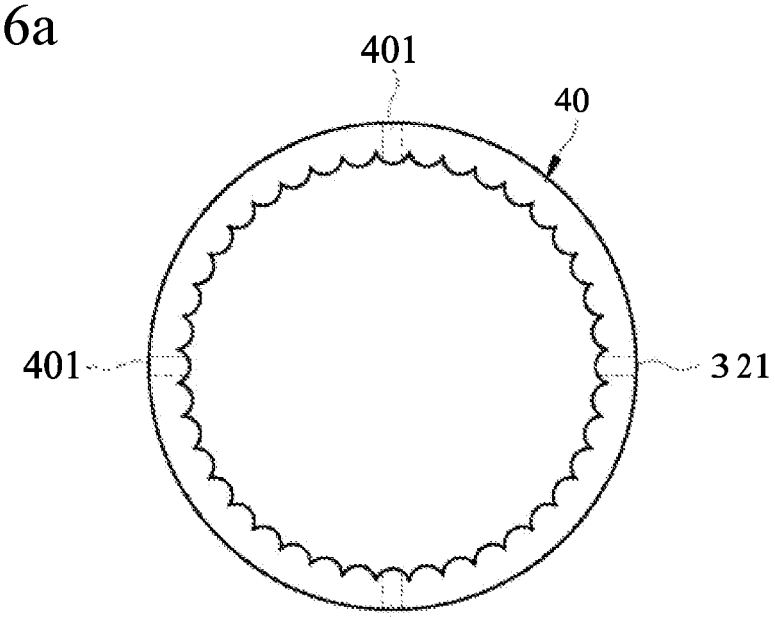
FIG. 6b is a top view showing the reflection chamber according to the present invention.
Figure 6C:
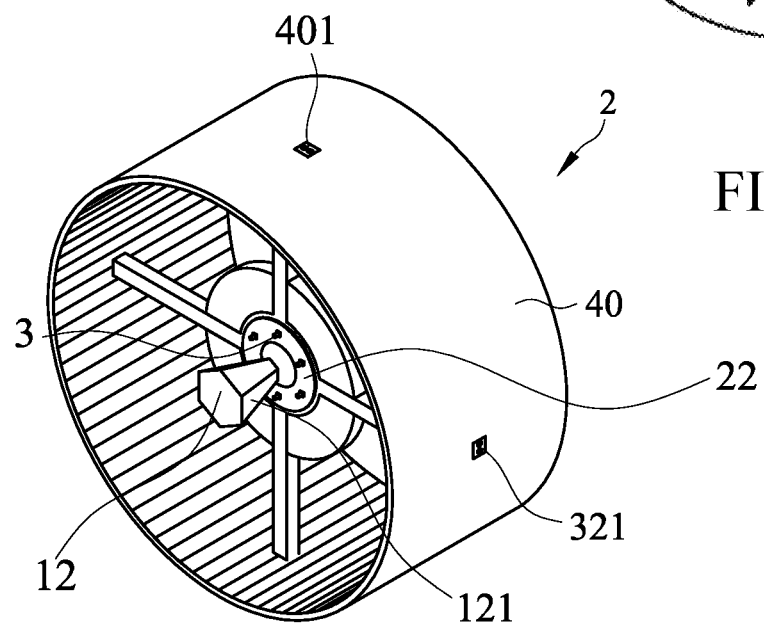
FIG. 6c is a schematic view showing a closed enhanced bundle beam UV LED ultraviolet light sweeping device according to Embodiment II of the present invention.

Embodiment II: A Closed Enhanced Bundle Beam UV LED Ultraviolet Light Sweeping Device Referring to FIGS. 6a-6c, FIG. 6a is a side elevational view showing a closed reflection chamber according to the present invention; FIG. 6b is a top plan view showing the closed reflection chamber according to the present invention; and FIG. 6c is a schematic view showing a closed enhanced bundle beam UV LED ultraviolet light sweeping device according to Embodiment II of the present invention.

As shown in FIG. 6a-6c, the closed enhanced bundle beam UV LED ultraviolet light sweeping device 2 comprises a closed reflection chamber 40. The closed reflection chamber 40 provides, as being preserved in advance, with holes 401 for mounting the mounting braces 32, and the electrical power inlet hole 321 connects the at least one bundle beam UV LED ultraviolet light bead 3 and the rotating device 10 and are fixed by means of screws. The internal wall of the closed reflection chamber 40 is a high-reflectivity aluminum layer. When electrical power source is activated, the electrical power inputs into the PCB 22, and the motor 11, and also the at least one (or more) bundle beam UV LED ultraviolet light bead(s) 3, is activated simultaneously to drive the polygonal multiple-reflective-surface aluminum mirror 12 to rotate therewith, and the at least one (or more) bundle beam UV LED ultraviolet light bead(s) 3 on the PCB 22 generates a light beam projecting toward the reflective surface 121 of the polygonal multiple-reflective-surface aluminum mirror 12, and a light beam of reflection is projected toward the closed reflection chamber 40 to be reflected by an aluminum mirror of the closed reflection chamber 40. The internal wall of the closed reflection chamber 40 is a column-shaped non-spherical pattern, and the column-shaped non-spherical pattern is perpendicular to the incident light. The column-shaped non-spherical pattern can be one of arc configuration, triangular configuration, or rectangular configuration. The behavior of light reflection of light being projected to a column-shaped non-spherical reflective surface, that is in accordance to the principles of Maddox rod as discovered by the inventor of present invention, is being applied here. Upon incidence onto the column-shaped non-spherical pattern, the reflection light forms secondary reflection light of which a meridian direction is in a direction perpendicular to the column-shaped non-spherical pattern, once again making radiation light overlapping within the operation region until being decayed to vanish, forming a high-dosage radiation beam region of homogeneous distribution, where the reflection light of the ultraviolet light strengthens radiation internally, while reduces radiation leaking out of the reflection chamber externally, to thereby reduce secondary contamination and to ensure protection of safety of users.

Embodiment III: Application of Embodiment II, a Closed Enhanced Bundle Beam UV LED Ultraviolet Light Sweeping Device, in Central Air Conditioning Referring to FIG. 7, FIG. 7 is a schematic view of Embodiment III of the present invention, showing the application of a closed enhanced bundle beam UV LED ultraviolet light sweeping device according to Embodiment II of present invention in central air conditioning.

Figure 7:
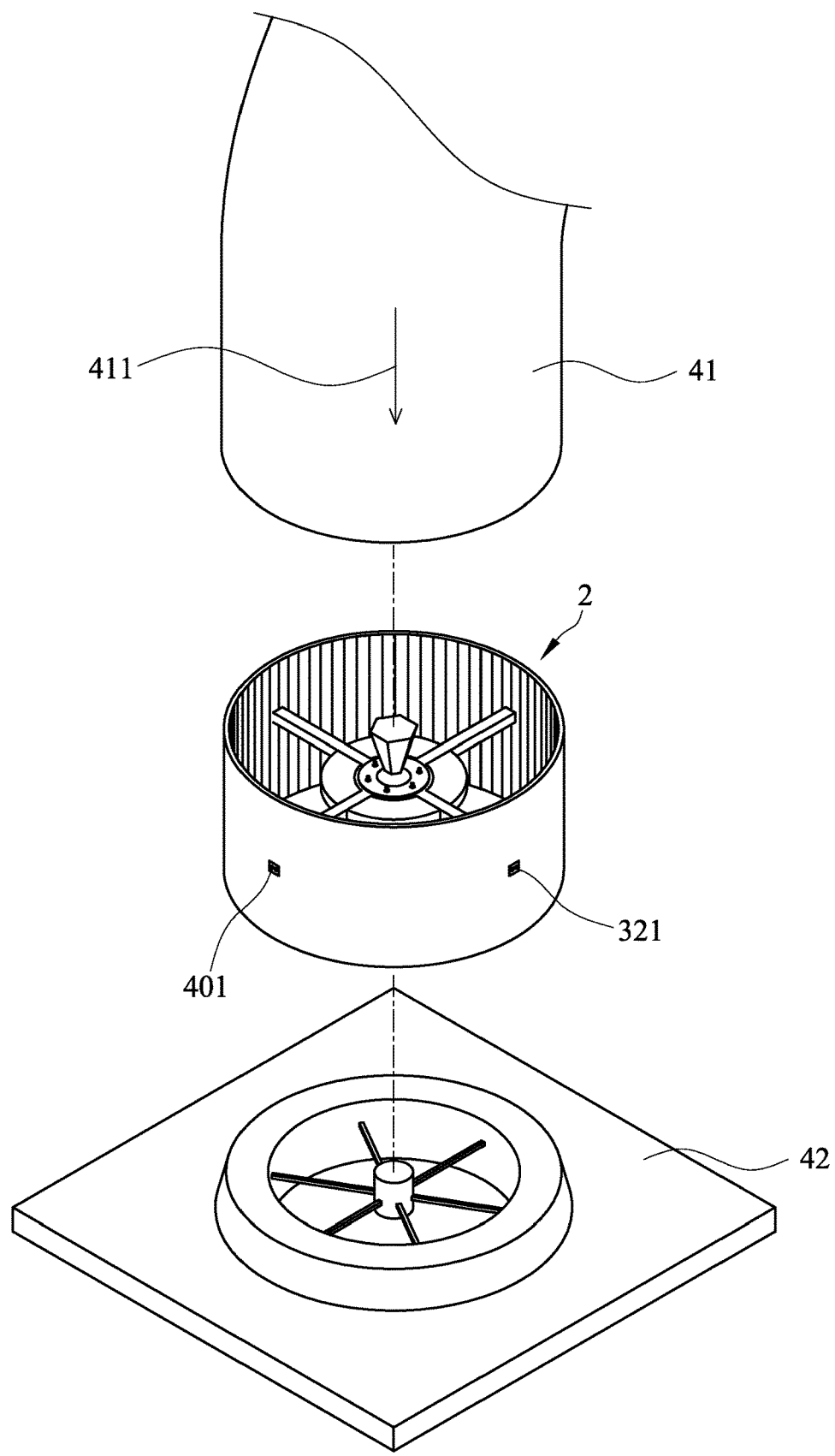
FIG. 7 is a schematic view showing a bundle beam UV LED ultraviolet light sweeping device according to Embodiment III of the present invention.

As shown in FIG. 7, the closed enhanced bundle beam UV LED ultraviolet light sweeping device 6c is mounted between a ventilation pipeline 41 and an air outlet 42 of an air conditioning system, so that when circulating air moves (in a direction indicated by an arrow 411) to enter, in a passive manner, into the closed enhanced bundle beam UV LED ultraviolet light sweeping device 6c, the motor 11 is activated to rotate, the bundle beam UV LED ultraviolet light bead 3 is turned on simultaneously, would realize sweeping with ultraviolet light of the UV LED of a wavelength of 250-285 nm, and the high radiation dosage suffices to quickly disinfect and sterilize viruses and to deodorize organic gases, and by means of air circulation realized with the air-conditioning system, disinfection and sterilization of viruses and purification of air, with assistance of removal of odors therefrom, can be achieved, for applications enclosed spaces, such as a central air conditioning device, an air-conditioner, a ship, an airplane, a car, a subway, a train.

Embodiment IV: A Lateral-Opening Enhanced Bundle Beam UV LED Ultraviolet Light Sweeping Device Referring to FIG. 8, FIG. 8 is a schematic view showing a bundle beam UV LED ultraviolet light sweeping device according to Embodiment IV of the present invention.

Figure 8:
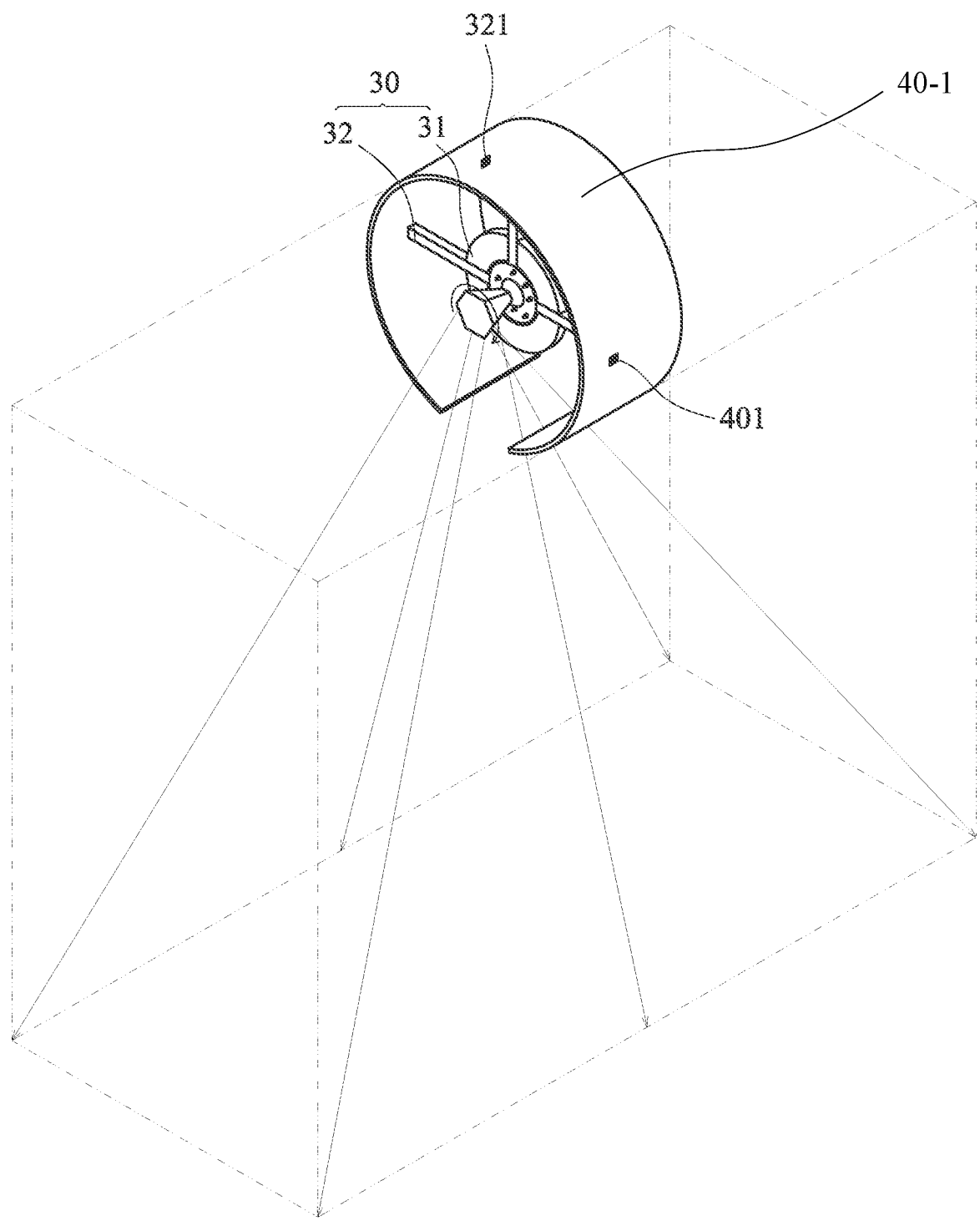
FIG. 8 is a schematic view showing a bundle beam UV LED ultraviolet light sweeping device according to Embodiment IV of the present invention.

As shown in FIG. 8, the bundle beam UV LED ultraviolet light sweeping device of the present invention shown in FIG. 2 may further comprise a lateral-opening type reflection chamber 40-1, which is opened at a lateral side or a circumference to form a partial opening, wherein the rotating device is disposed inside the lateral opening type reflection chamber 40-1, and the polygonal multiple-reflective-surface aluminum mirror 12 is connected to the spindle 111 of the motor 11 to be driven by the motor 11 to rotate, wherein one of the mounting braces 32 is an electrical power inlet hole 321 for connection with the PCB 22. Embodiment IV may be used for surface sterilization for medical equipment, fresh-keeping and preservation for foods, wherein a box shown with phantom lines indicates a possible container for surface sterilization with a laterally opened enhanced bundle beam UV LED ultraviolet light sweeping device according to Embodiment IV of the present invention installed.

Embodiment V: A Lateral-Opening Enhanced Bundle Beam UV LED Ultraviolet Light Sweeping Device According to Embodiment IV of the Present Invention Referring to FIG. 9a, FIG. 9a is a schematic view showing a bundle beam UV LED ultraviolet light sweeping device according to Embodiment V of the present invention; and FIG. 9b is a schematic view showing an elongated irregular-shaped polygonal column configured reflective surface aluminum mirror according to the present invention.

Figure 9A:
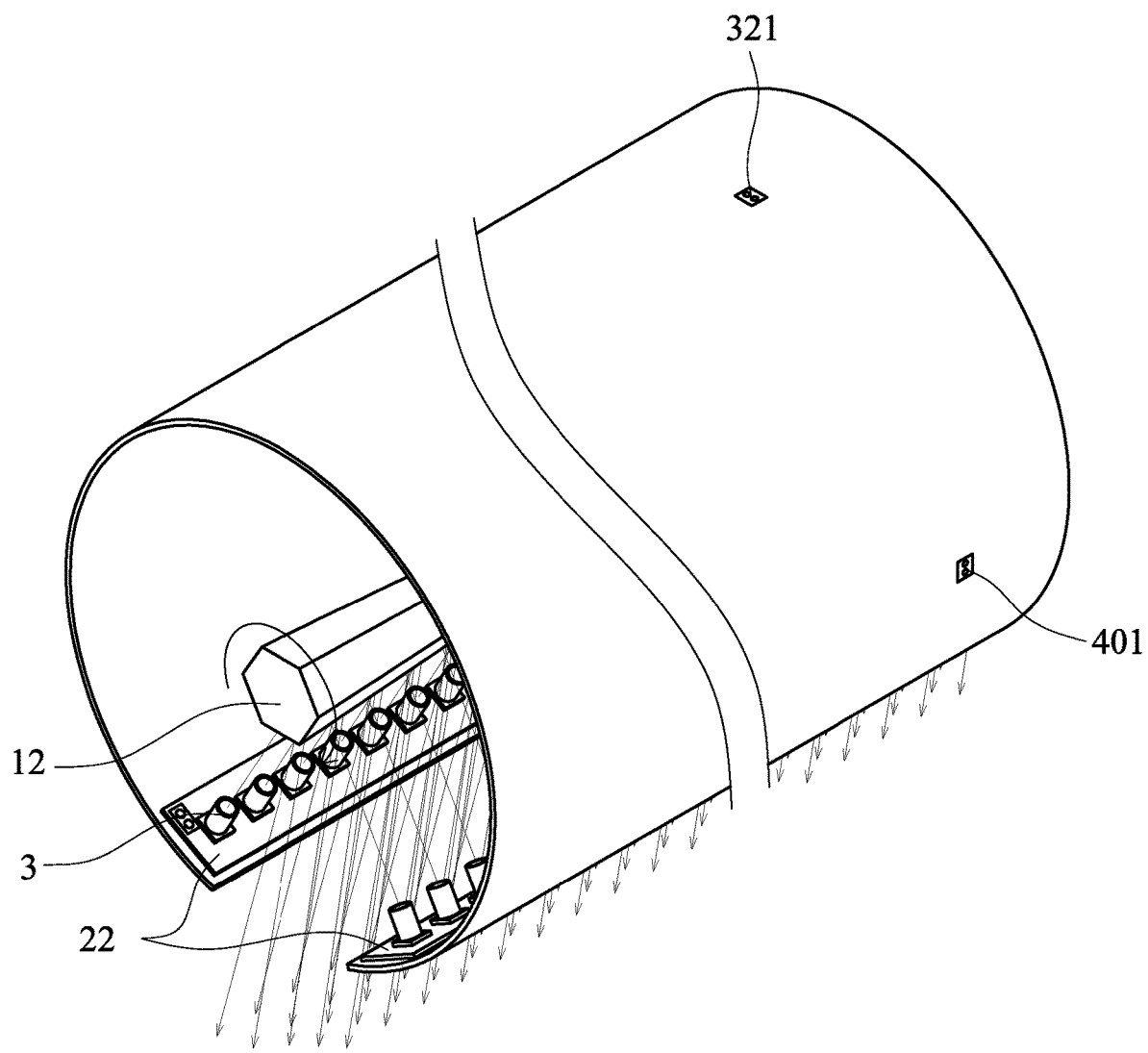
FIG. 9a is a schematic view showing a bundle beam UV LED ultraviolet light sweeping device according to Embodiment V of the present invention.
Figure 9B:
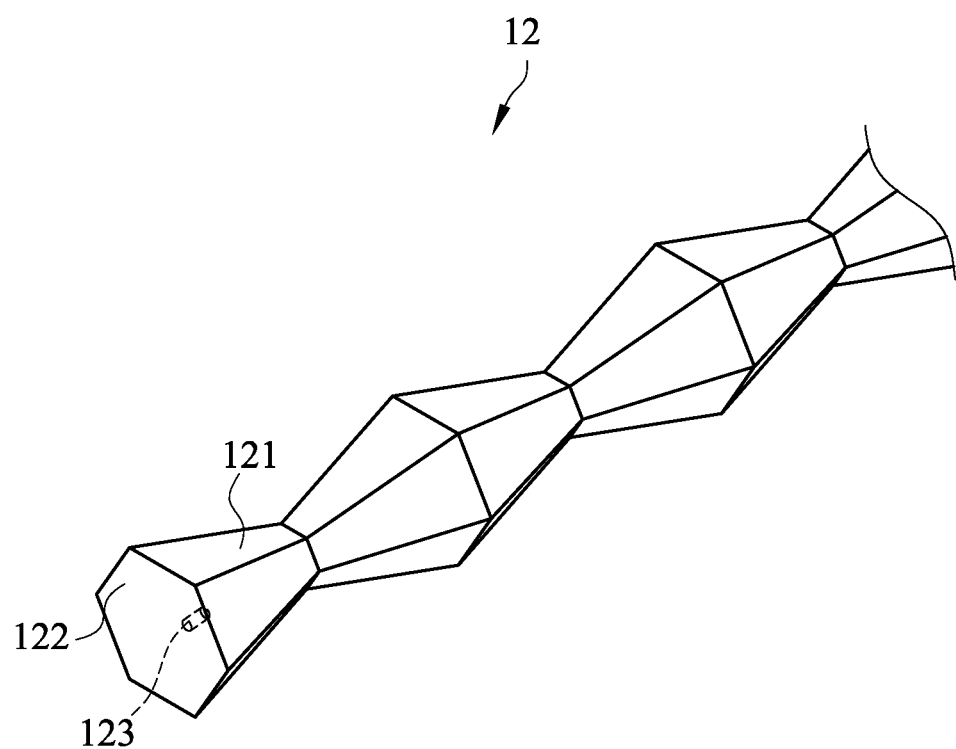
FIG. 9b is a schematic view showing a polygonal irregular-shaped elongated column configuration reflective surface aluminum mirror according to the present invention.

As shown in FIGS. 9a and 9b, the bundle beam UV LED ultraviolet light sweeping device of the present invention shown in FIG. 2 includes the lateral-opening type reflection chamber 40-1, wherein the rotating device 10 is disposed inside the lateral-opening type reflection chamber 40-1. The polygonal multiple-reflective-surface aluminum mirror 12 is a multiple-angled multiple-sided column shaped reflective surface aluminum mirror or a multiple-angled irregular shaped multiple-sided column shaped reflective surface aluminum mirror of FIG. 9b, and the polygonal multiple-reflective-surface aluminum mirror 12 is connected to the spindle 111 of the motor 11 to be driven by the motor 11 to rotate. Further, the elongated PCB 22 is correspondingly disposed inside the lateral-opening type reflection chamber 40-1 at a location adjacent to the opening. A plurality of bundle beam UV LED ultraviolet light beads 3 are mounted on the PCB 22. Further, the fixing base 30 fixes the motor 11 and the polygonal multiple-reflective-surface aluminum mirror 12 of the rotating device, and the plurality of mounting braces 32 are fixed to the lateral-opening type reflection chamber 40-1, wherein one of the mounting braces 32 is an electrical power inlet hole 321 for connection with the PCB 22. The current Embodiment V employs bundle beam UV LED ultraviolet light bead of a wavelength of 350-405 nm. By means of the polygonal multiple-reflective-surface aluminum mirror 12 radiation light is projected outward through the opening, and the outward-projected radiation light beam is perpendicular to a surface of UV resin to be polymerized and cured, back-and-forth moving upwards and downward, leftward and rightwards, for sweeping to form a high dosage radiation light beam region for conducting a curing process for polymerization and curing of UV resin in a large area, wherein the photo-initiators contained in the UV resin is subject to the high radiation energy to fast polymerize and harden, without being overheated and scorching. The bundle beam UV LED ultraviolet light sweeping method and the device thereof according to the present invention are such that the radiation light is projected in a direction toward the opening for being perpendicular to the surface of UV resin, and activation of the electrical power to carry out back-and-forth movement leftwards and rightwards for sweeping to conduct an operation of curing and hardening of UV resin in a large area, so as to fast move the liquid state UV resin and to gain high radiation energy for fast polymerization and curing, without overheating and thus scorching, radiation energy being low making it hard for vaporization of molecules, relatively less contamination being made on the bead, leading to extension of bead service life, good for application in business requiring photo curing.

Embodiment VI: Enhanced Bundle Beam UV LED Ultraviolet Light Sweeping Device with Air Extraction or Air Delivering Power Referring to 10, FIG. 10 is a schematic view showing a bundle beam UV LED ultraviolet light sweeping device according to Embodiment VI of the present invention.

Figure 10:
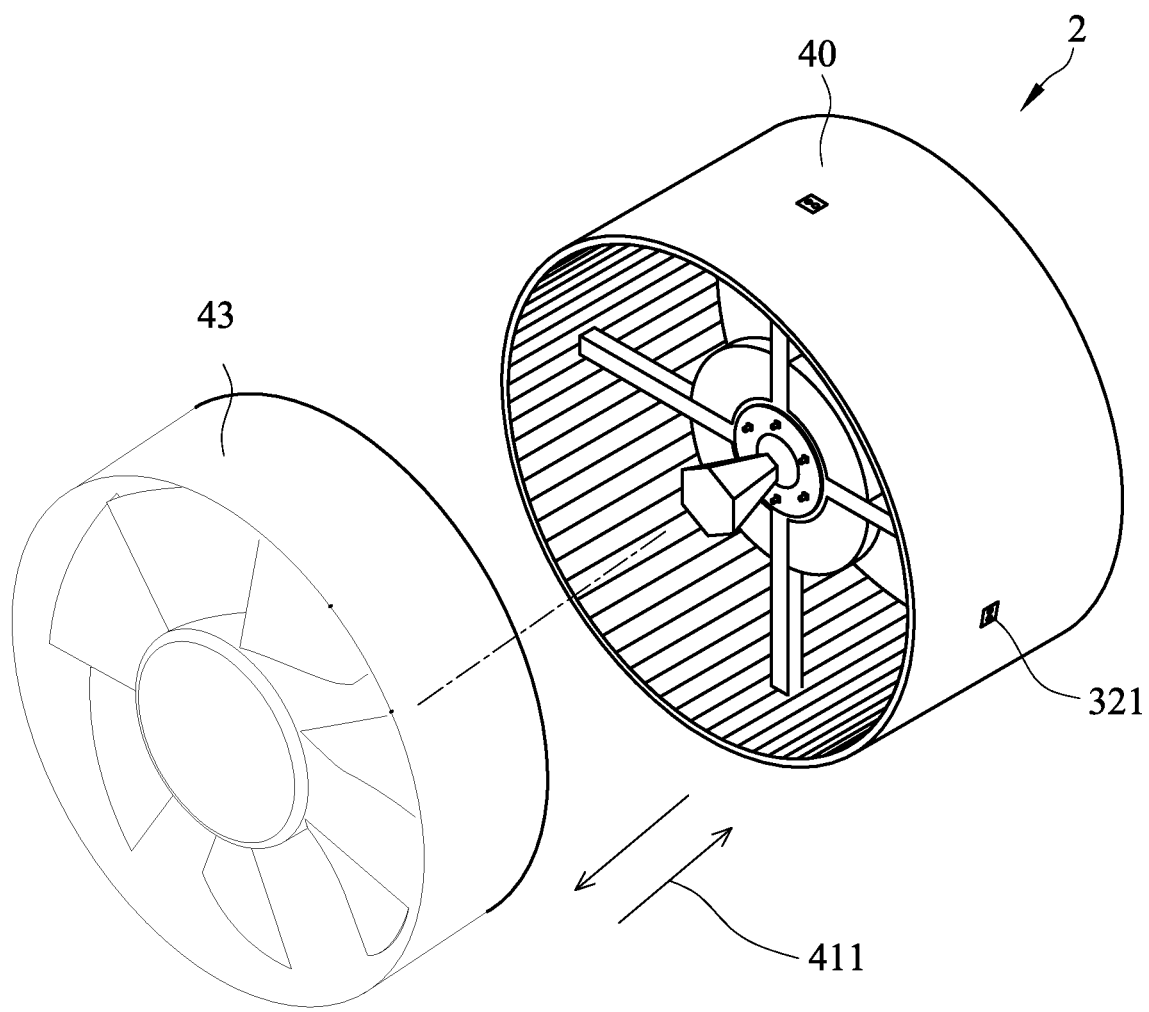
FIG. 10 is a schematic view showing a bundle beam UV LED ultraviolet light sweeping device according to Embodiment VI of the present invention.

As shown in FIG. 10, the reflection chamber 40 of the closed enhanced bundle beam UV LED ultraviolet light sweeping device 2 of FIG. 6c is connected to an air drawing/blowing machine 43. The reflection chamber 40 includes, in the interior thereof, column shaped successive strip pattern, which functions to prevent leaking of radiation. When the radiation light gets incident onto the non-spherical column shaped reflective mirror, the reflection light forms meridian light in a direction perpendicular to the column shape, making it hard to leak, to thereby reduce secondary contamination, while air in the middle is driven by the air drawing/blowing machine to flow through the sweeping device, with the direction of the air flow being indicated by an arrow 411, to actively carry out sterilization and disinfection of air, making it particularly suitable for a large open space, such as a hotel, an exhibition site, a school, a department store, and a shopping mall as a middle space active sterilization and disinfection device.

Embodiment VII: Enhanced Bundle Beam UV LED Ultraviolet Light Sweeping Device for Water Disinfection Referring to FIG. 11, FIG. 11 is a schematic view showing a bundle beam UV LED ultraviolet light sweeping device according to Embodiment VII of the present invention.

Figure 1:
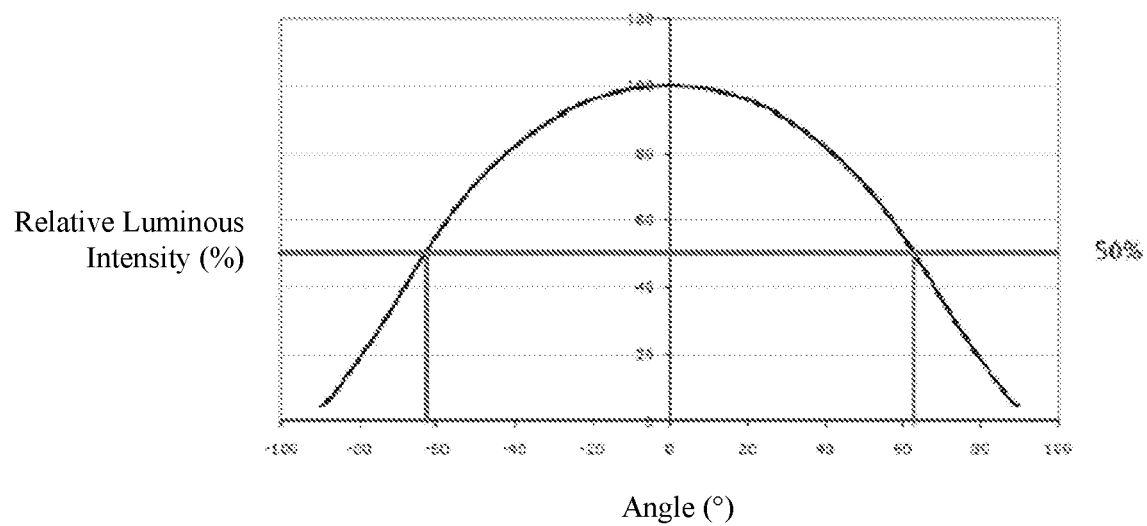
FIG. 1 is a plot demonstrating a relationship between luminance at a center axis and luminance of 50% decay.
Figure 11:
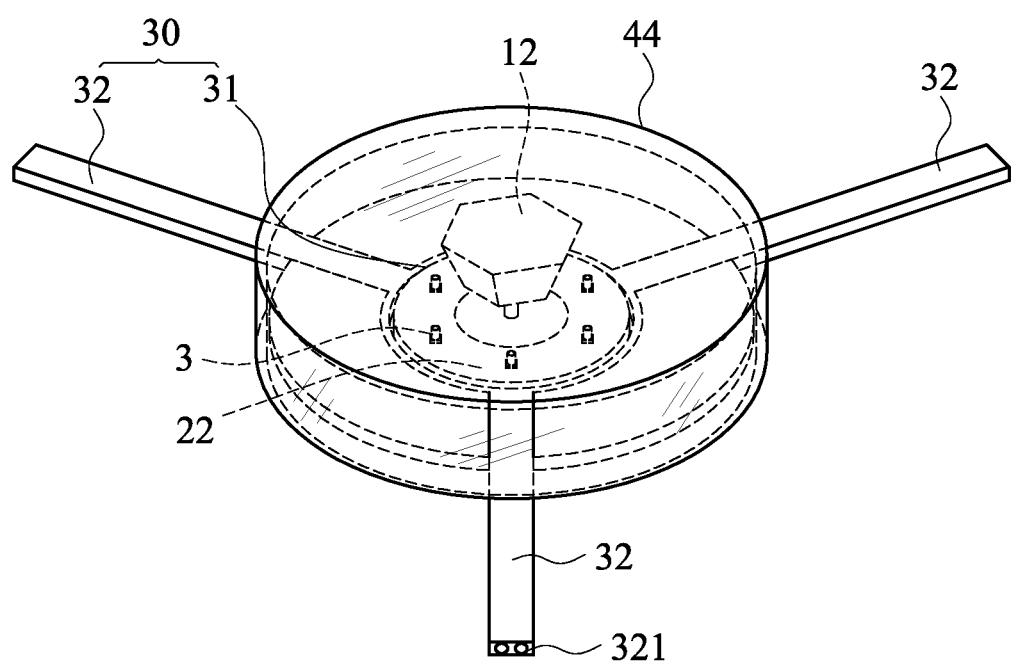
FIG. 11 is a schematic view showing a bundle beam UV LED ultraviolet light sweeping device according to Embodiment VII of the present invention.

As shown in FIG. 11, the bundle beam UV LED ultraviolet light sweeping device according to the present invention may further comprises a quartz glass sleeve 44 that hermetically house the rotating device 10 and the UV LED bundle beam light source assembly 20 on the fixing base main body 31, wherein the quartz glass sleeve 44 servers water resistance and water protection for the bundle beam UV LED ultraviolet light sweeping device 1 and also as an observation window through which light transmits. The hermetically sealed, water-resistant bundle beam UV LED ultraviolet light sweeping device of FIG. 1 may be used as in applications for disinfection in water. High radiation dosage suffices for fast eliminating bacteria, for conducting disinfection and sterilization for still or flowing water, for applications of disinfection of drinking water, swimming pools, aquafarming sites and so on for disinfection and sterilization.

Embodiment VIII: A Flow Chart Showing the Sweeping Method of a Bundle Beam UV LED Ultraviolet Light Sweeping Device Referring to FIG. 12 is a flow chart showing the sweeping method of a bundle beam UV LED ultraviolet light sweeping device according to Embodiment VIII of the present invention.

Figure 12:
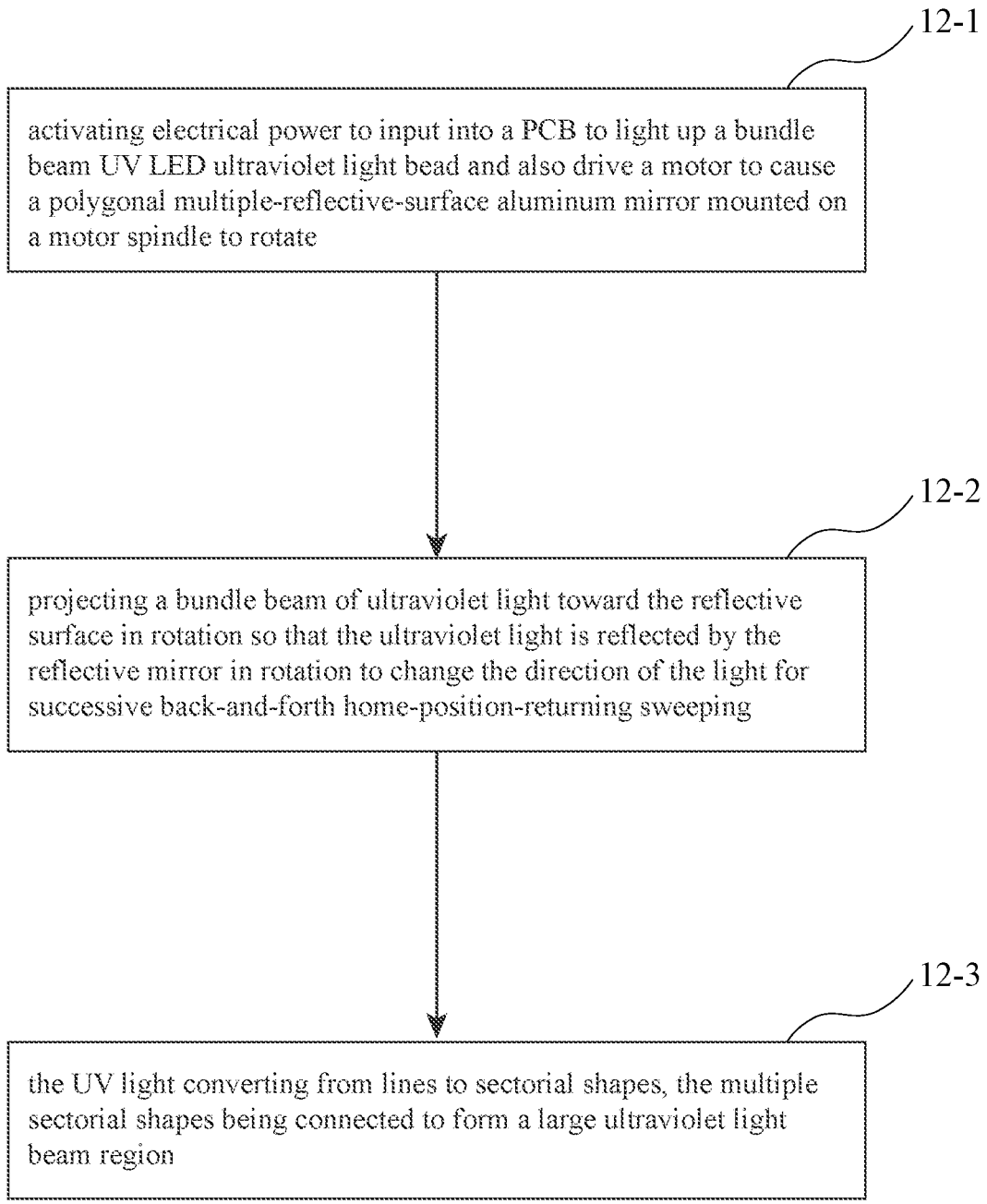
FIG. 12 is a flow chart illustrating a bundle beam UV LED ultraviolet light sweeping method according to the present invention.

As shown in FIG. 12, the scanning method of a bundle beam UV LED ultraviolet light comprises of step 1(12-1): providing a printed circuit board (PCB) 22 with an electrical power supply that is conducted in through an electrical power inlet hole 321 and activating the electrical power to light up at least one bundle beam UV LED ultraviolet light bead 3 on the PCB 22, and also driving a rotating device 10 to drive a polygonal multiple-reflective-surface aluminum mirror 12 on a spindle 111 of a motor 11 to rotate; step 2(12-2): ultraviolet light emitting from the at least one bundle beam UV LED ultraviolet light bead 3 is projected to a reflective surface 121 of the polygonal multiple-reflective-surface aluminum mirror 12, wherein it is known from the principle of reflection that when an incident angle is constantly changing during the rotation; step 3(12-3): an angle of reflection light orderly changes direction, the successive back-and-forth home-position-returning for positional light emitting provided by present invention allows reflection light to form a sectorial shaped radiation light surface whereof the area is increased with a distance thereof toward the outside, connecting multiple number of such sectorial shaped radiation light surface results in enlarged working area of ultraviolet light radiation light beam.

Above descriptions of the various embodiments of the present invention have been presented for the purpose of illustration, are not intended to be exhaustive or limited to the embodiments disclosed. Many modifications and variations within the scope and spirit of the described embodiments hence the present invention will be apparent to those of ordinary skill in the art. These modifications and/or variations, therefore, are within the right of the present invention.

I claim:

1. A bundle beam ultraviolet light-emitting diode (UV LED) ultraviolet light sweeping method, the method comprising the following steps:

Step 1: providing electrical power supplied into a printed circuit board (PCB) and activating the electrical power to light up a bundle beam UV LED ultraviolet light bead, and simultaneously driving a rotating device to drive a polygonal multiple-reflective-surface aluminum mirror on a motor spindle to rotate; step 2: projecting a bundle beam of ultraviolet light toward the polygonal multiple-reflective-surface aluminum mirror in rotation, and the ultraviolet light being reflected by the polygonal multiple-reflective-surface aluminum mirror in rotation to start sweeping; step 3: reflected ultraviolet light orderly changes direction due to continuous back-and-forth home-position-returning sweeping converting UV light projection from a line into a sectorial area, wherein the sectorial shapes can further be connected to form a larger ultraviolet light radiation light beam area.

2. A bundle beam UV LED ultraviolet light sweeping device, comprising at least: a rotating device, the rotating device providing a motor, a spindle of the motor being mounted with a polygonal multiple-reflective-surface aluminum mirror; an UV LED bundle beam light source assembly, the UV LED bundle beam light source assembly comprising at least one bundle beam UV LED ultraviolet light bead and a PCB, the bundle beam UV LED ultraviolet light bead being fixed on the PCB; a fixing base, the fixing base comprising a main body serving as a platform for carrying components and a plurality of mounting braces.

3. The bundle beam UV LED ultraviolet light sweeping device according to claim 2, further comprising a reflection chamber, the fixing base being fixed inside the reflection chamber, an internal wall of the reflection chamber being high reflective aluminum layer, the internal wall of the reflection chamber comprising a column shaped non-spherical pattern, the column shaped non-spherical pattern being perpendicular, in direction, to incident light, the column shaped non-spherical pattern can be either one of an arc configuration, a triangular configuration, or a rectangular configuration.

4. The bundle beam UV LED ultraviolet light sweeping device according to claim 3, further comprising an air outlet and a ventilation pipeline, the air outlet and the ventilation pipeline being respectively arranged at two sides of the reflection chamber.

5. The bundle beam UV LED ultraviolet light sweeping device according to claim 3, further comprising an air drawing/blowing device, the air drawing/blowing device being fixed at one side of the reflection chamber.

6. The bundle beam UV LED ultraviolet light sweeping device according to claim 2, further comprising a quartz glass sleeve, the quartz glass sleeve being adhered by silicone on the main body of the fixing base.

7. The bundle beam UV LED ultraviolet light sweeping device according to claim 2, wherein the bundle beam UV LED ultraviolet light bead includes an ultraviolet light bead of 250-405 nm UV LED primary encapsulation, added with a hollow metal tube of secondary encapsulation adhered by silicone; with a height of the hollow metal tube ranging from 1.2 mm to 20 mm.

8. The bundle beam UV LED ultraviolet light sweeping device according to claim 7, wherein the secondary encapsulation uses a hollow metal tube having an inside-rectangular and outside-rectangular configuration, or an inside-circular and out-side circular configuration, or an inside-circular and outside-rectangular configuration, and the material of the hollow metal tube can be one of aluminum, copper, nickel, tin, or a metal coated with aluminum powder.

9. The bundle beam UV LED ultraviolet light sweeping device according to claim 8, wherein the hollow metal tube of the secondary encapsulation has an inside surface is either a successive internal corrugated arc-configuration reflective mirror, or a successive internal corrugated triangular-configuration reflective mirror, or a successive internal corrugated rectangular-configuration reflective mirror, wherein the direction of the successive corrugation is perpendicular to the direction of light projection, and the material of the hollow metal tube can be either aluminum, copper, nickel, tin, or a metal coated with aluminum powder.

10. The bundle beam UV LED ultraviolet light sweeping device according to claim 2, wherein the polygonal multiple-reflective-surface aluminum mirror comprises three or more reflective surfaces, the polygonal multiple-reflective-surface aluminum mirror being formed of plastics injection molding, followed by coating of metallic aluminum by means of vacuum electroplating, or being formed by direct machining or processing metallic aluminum, and the polygonal surface forms a θ included angle with respect to each of the reflective surfaces, the θ included angle being either a θ angle identical for each of the reflective surfaces or a θ angle different for each of the reflective surfaces.

11. The bundle beam UV LED ultraviolet light sweeping device according to claim 2, wherein the motor can be either an alternate-current motor, a direct-current motor, a brushless motor, or a stepping motor.

12. The bundle beam UV LED ultraviolet light sweeping device according to claim 2, wherein the PCB of the UV LED bundle beam light source assembly can be either a polymer PCB, a metal PCB, or a ceramic PCB.

13. The bundle beam UV LED ultraviolet light sweeping device according to claim 2, wherein the main body and the mounting braces can be formed by a unitary body or are formed by separate parts, and one of the mounting braces is provided with an electrical power inlet hole, and the material of the fixing base can be either an inorganic material coated with metallic aluminum, an inorganic material, or a metallic material.

14. The bundle beam UV LED ultraviolet light sweeping device according to claim 2, further comprising a lateral-opening type reflection chamber, the lateral-opening type reflection chamber has an opening on its lateral side, radiation light being outwardly projected through the opening.

15. The bundle beam UV LED ultraviolet light sweeping device according to claim 14, wherein the polygonal multiple-reflective-surface aluminum mirror can be either a polygonal multiple-sided column shaped reflective surface aluminum mirror or a polygonal multiple-sided irregular column shaped reflective surface aluminum mirror.

16. The bundle beam UV LED ultraviolet light sweeping device according to claim 14, wherein the bundle beam UV LED ultraviolet light bead has a wavelength of 285-350 nm for cultivation of fungi and mushrooms and phototherapy.

17. The bundle beam UV LED ultraviolet light sweeping device according to claim 14, wherein the bundle beam UV LED ultraviolet light bead has a wavelength of 350-405 nm for photopolymerization and curing of a UV resin.

18. The bundle beam UV LED ultraviolet light sweeping device according to claim 2, wherein the bundle beam UV LED ultraviolet light bead has a wavelength of 250-285 nm for surface sterilization.

* * * * *